(12) United States Patent
Mitschke

(10) Patent No.: US 7,536,219 B2
(45) Date of Patent: May 19, 2009

(54) 4D IMAGING WITH A C-ARM X-RAY SYSTEM

(75) Inventor: Matthias Mitschke, Walnut Creek, CA (US)

(73) Assignee: Siemens Aktiengesellschaft, Munich (DE)

( * ) Notice: Subject to any disclaimer, the term of this patent is extended or adjusted under 35 U.S.C. 154(b) by 557 days.

(21) Appl. No.: 11/036,307

(22) Filed: Jan. 14, 2005

(65) Prior Publication Data

US 2005/0201515 A1   Sep. 15, 2005

Related U.S. Application Data

(60) Provisional application No. 60/546,573, filed on Feb. 20, 2004.

(51) Int. Cl.
*A61B 5/05* (2006.01)
*A61B 6/00* (2006.01)
(52) U.S. Cl. ........................ 600/425; 600/431
(58) Field of Classification Search ............... 600/425, 600/431; 378/8, 15, 62
See application file for complete search history.

(56) References Cited

U.S. PATENT DOCUMENTS

| 4,413,620 | A | * | 11/1983 | Tucker | 128/869 |
|---|---|---|---|---|---|
| 5,997,883 | A | * | 12/1999 | Epstein et al. | 324/306 |
| 6,522,712 | B1 | * | 2/2003 | Yavuz et al. | 378/4 |
| 6,535,570 | B2 | | 3/2003 | Stergiopoulos et al. | |
| 6,621,889 | B1 | * | 9/2003 | Mostafavi | 378/65 |
| 6,665,370 | B2 | | 12/2003 | Bruder et al. | |
| 6,811,313 | B2 | | 11/2004 | Graumann et al. | |
| 2003/0007675 | A1 | * | 1/2003 | Schmidt et al. | 382/132 |

* cited by examiner

*Primary Examiner*—Eric F Winakur
*Assistant Examiner*—Michael T Rozanski
(74) *Attorney, Agent, or Firm*—Schiff Hardin LLP

(57) ABSTRACT

The present invention utilizes external motion sensors to determine a periodic motion of a patient being examined when generating a series of projected images with a C-arm X-ray device. Three-dimensional images are assembled based on the position information provided by the external motion sensors, and a corresponding four-dimensional image is constructed therefrom.

7 Claims, 3 Drawing Sheets

4D IMAGING WITH A C-ARM X-RAY SYSTEM

CROSS REFERENCE TO RELATED APPLICATIONS

The present application claims the benefit of U.S. Provisional Application No. 60/546,573, filed Feb. 20, 2004, herein incorporated by reference.

BACKGROUND

The present invention concerns methods and systems for medical imaging of an examination subject.

The technical problem to be solved with this invention is the imaging of parts of the patient anatomy that are moving periodically during the acquisition, for instance, due to patient breathing. In computer tomography (CT) applications, four-dimensional (4D) methods are gaining interest. Using external sensors (e.g., spirometers, etc.) the image information that is continuously being acquired is associated with position information and organized accordingly. Several three-dimensional (3D) volumes can be reconstructed corresponding to several points within the periodical motion of the patient anatomy. Not only in imaging but also in radiation therapy such methods are being used in order to optimize and reduce the radiation that is applied to the patients. Also for angiography applications, such methods would be very advantageous, as this would enable a 3D visualization of blood flow in 3D.

3D reconstruction of objects in motion using X-ray C-arm systems up to now have been limited to a few applications. For using such a system on a region of a patient that is in motion due to respiration, one possibility is to use a C-arm imaging device that can image the whole patient anatomy in a breath hold (10-20 sec), but this depends on the patient condition. This can he achieved with stationary C-arms moving with a speed up to 40 degrees/sec. Using mobile X-ray C-arms in the operating room on anesthetized patients allows breathing motion to be reduced to an absolute minimum for, e.g., the one minute of time that it takes for image acquisition.

SUMMARY

The present invention does not rely on such breath-holding or motion-stabilizing activities, but rather is able to utilize periodic motion advantageously by the use of external motion sensors that are able to provide position and motion information along with the measurement information so that image data sets can be reconstructed and analyzed based on a particular portion of a motion cycle.

DESCRIPTION OF THE DRAWINGS

Various embodiments of the invention are described below and are illustrated by the following drawings.

DETAILED DESCRIPTION OF THE PREFERRED EMBODIMENTS

Figure 1:
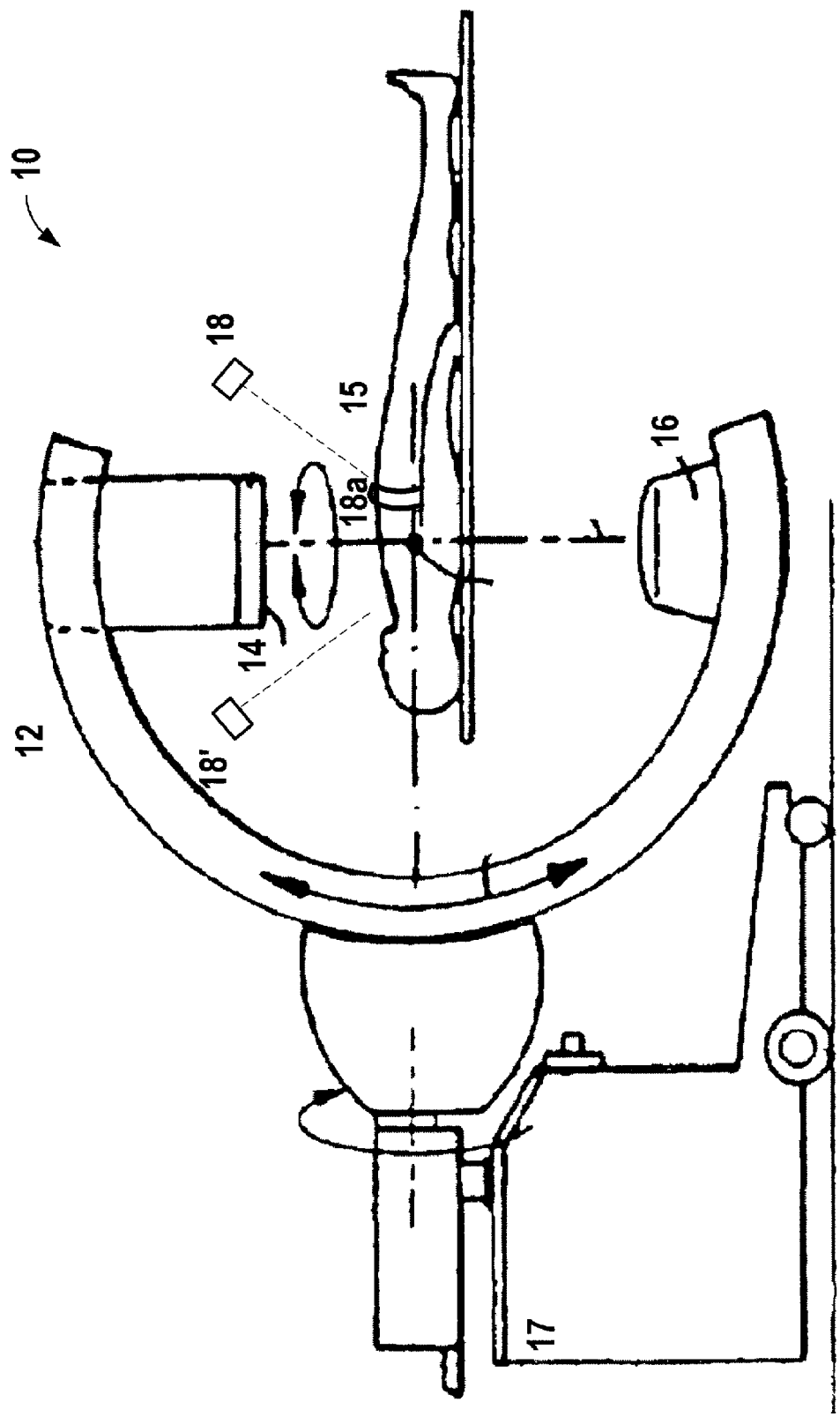
FIG. 1 is a pictorial schematic side view of a C-arm X-ray system having external position and motion sensors.

As illustrated in FIG. 1, a C-Arm X-ray/irradiation system 10 is shown in which a C-arm 12 comprises an x-ray or radiation source 16 and detector 14 configured to irradiate a patient 15 and provide image information to a processor 17 for analysis.

According to an embodiment of the invention, external sensors 18, 18', 18a are provided in order to measure the position and motion (such as breathing) of the patient 15 in order to assign to each image a time stamp. The external sensors may be, e.g., image based cameras 18, 18' or a pressure belt 18a used to detect abdomen pressure against such a belt during a breathing cycle. The invention is not limited to the use of image devices 18, 18' or pressure belt 18a, but comprises any device that is able to determine motion or position information of a subject or portion of a subject. FIGS. 2A-D illustrate this approach in an embodiment where the motion is breathing related.

Figure 2A:
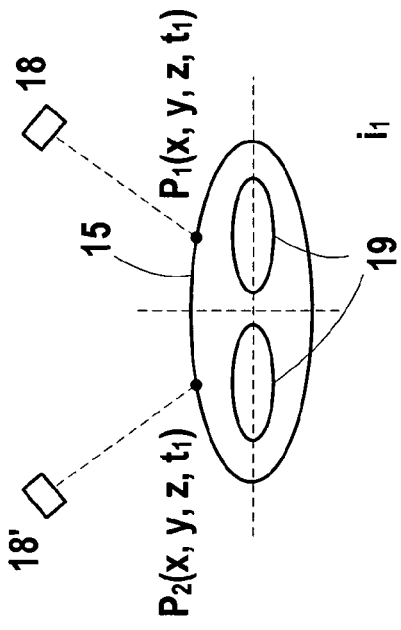
FIG. 2 is a cross-sectional pictorial view of a chest area of a patient showing the sensors.
Figure 2B:
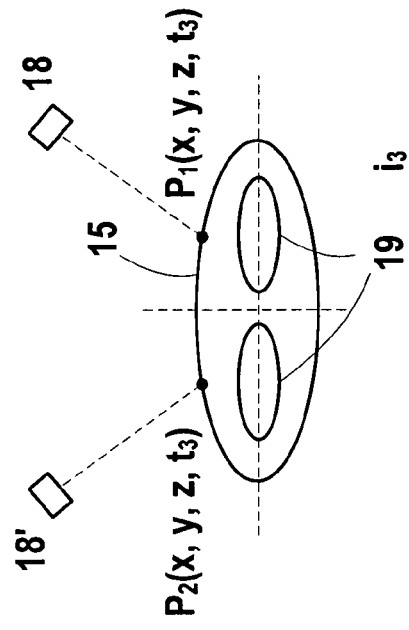

In FIG. 2A, a cross-section of the patent's 15 chest area is shown with the lungs 19 in an empty (exhaled) state, which, for the breathing periodic motion, could be considered as $\theta=0°$. The motion detectors 18, 18' determine that this is the $\theta=0°$ position by examining, e.g., point information $P_1(x, y, z, t_0)$, $P_2(x, y, z, t_0)$ located on the body, with image $i_0$ shown. When the lungs 19 are partially filled during the inhale portion of the cycle, corresponding with a periodic motion position of, e.g., $\theta=90°$ (FIG. 2B), the motion detectors 18, 18' are able to make this determination by examining the point information $P_1(x, y, z, t_1)$, $P_2(x, y, z, t_1)$ located on the body, with image $i_1$ shown.

Figure 2C:
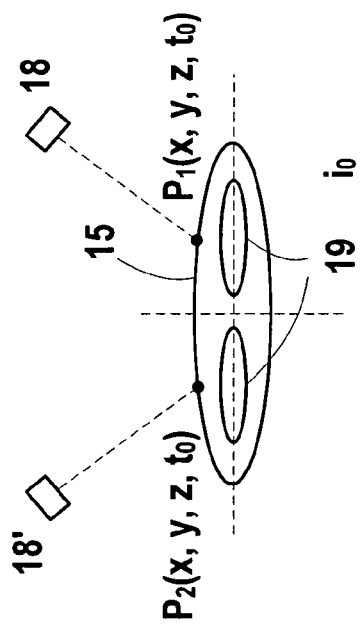
Figure 2D:
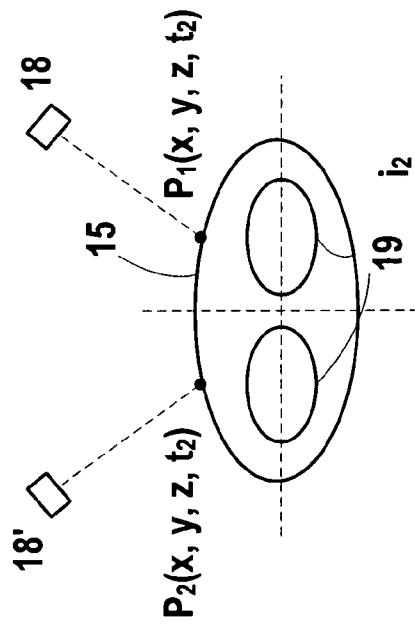

Correspondingly, as illustrated in FIG. 2C when the lungs 19 are completely filled, corresponding with a periodic motion position of, e.g., $\theta=180°$, the motion detectors 18, 18' are able to make this determination by examining the point information $P_1(x, y, z, t_2)$, $P_2(x, y, z, t_2)$ located on the body, with image $i_2$ shown. When the lungs 19 are partially emptied during the exhale portion of the cycle, corresponding with a periodic motion position of, e.g., $\theta=270°$ (FIG. 2D), the motion detectors 18, 18' are able to make this determination by examining the point information $P_1(x, y, z, t_3)$, $P_2(x, y, z, t_3)$ located on the body, with image $i_3$ shown.

Figure 3:
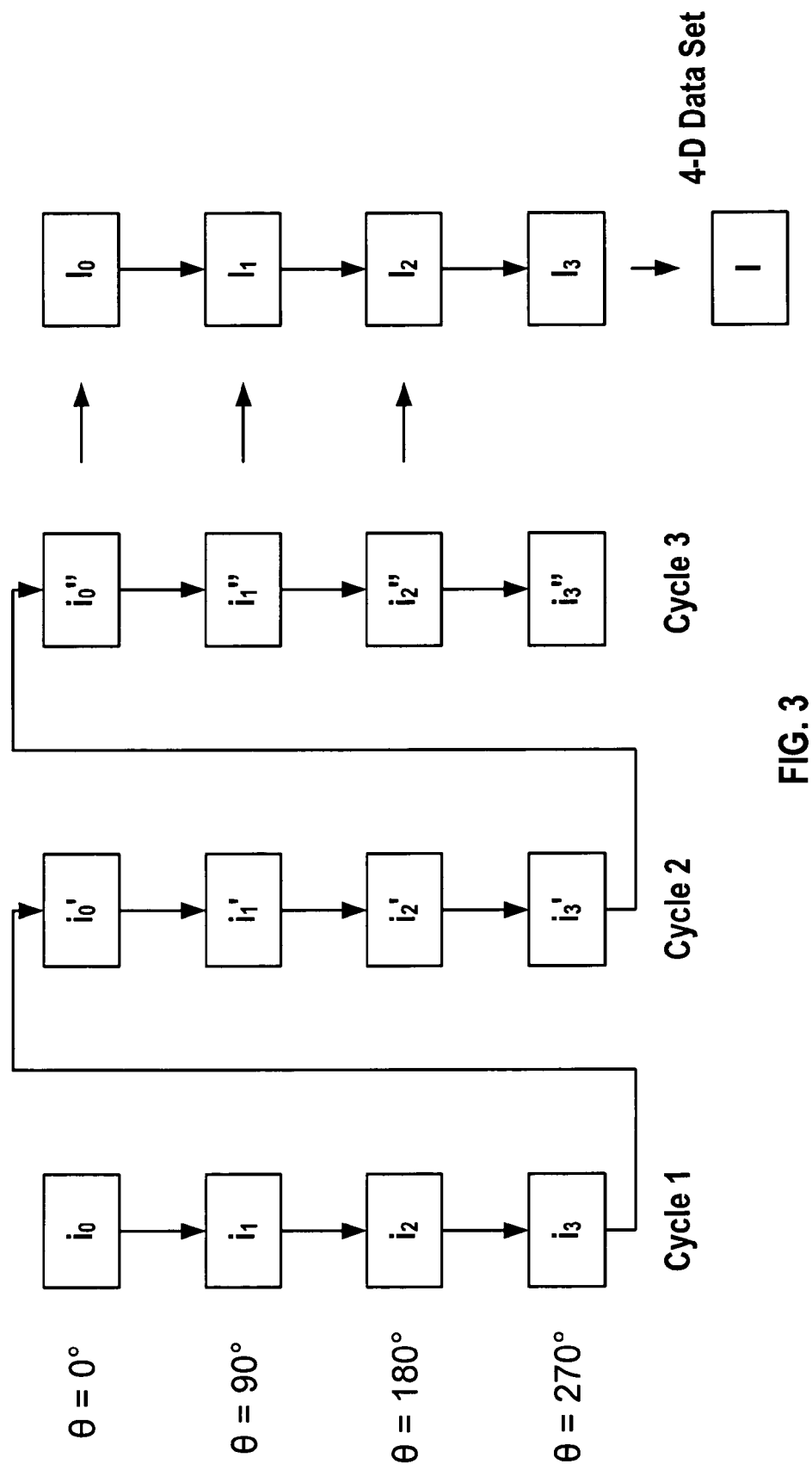
FIG. 3 is a sequence diagram showing the imaging over three motion cycle periods.

The imaging over three motion cycles is illustrated in FIG. 3, with Cycle 1 representing the imaging from FIGS. 2A-D. It can be seen that images $i_{0-3}$ are acquired in Cycle 1, each corresponding to particular phase of the motion cycle. The images $i_0'$-$i_3'$ are acquired in Cycle 2, again corresponding to a particular phase of the motion cycle and this process is repeated again for Cycle 3 producing the images $i_0''$-$i_3''$.

This operation allows one to collect all images out of the complete image series that have been acquired at a certain part of the motion cycle. All images belonging to one part of the motion cycle, e.g., for $\theta=90°$, $i_1$, $i_1'$ and $i_1''$ are reconstructed into 11 independently from the rest. They represent a 3D reconstruction of the patient anatomy for that particular part of the breathing cycle $\theta=90°$. A post-processing using state-of-the-art interpolation techniques (such as morphing) allows the creation of a 4D dataset $I_{0-3}$ from the separately reconstructed 3D reconstructions.

The implementation of the above-described technique is very simple and straightforward. Instead of triggering the acquisition of the C-arm 12, which would result in a complicated synchronization and geometry calibration procedure, it is suggested to use the inverse approach. The signals of the C-arm 12 (C-arm, flat panel/image intensifier) can be read out by the processor 17 and, together with the signal from the motion monitoring device 18, 18', 18a a time stamp is generated for each projection image that corresponds it with a part of the motion cycle.

After image acquisition is complete, the image dataset $i_0$-$i_3''$ is split into sub image datasets $i_0$-$i_0''$ to $i_3$-$i_3''$ to perform the independent reconstructions for the different parts of the motion cycle. After this process is finished, the 4D dataset I can be created from the several 3D volumes $I_0$-$I_3$ using known techniques. What is significant is that the image reconstruction is based on information related to the position within a cycle during a continuous acquisition of image data.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A method for creating a four-dimensional image of a, subject comprising:
    from a subject exhibiting uninterrupted periodic external motion, detecting position information representing the uninterrupted periodic external motion of the subject utilizing external position or motion sensors, said external periodic motion comprising successive phases;
    with a C-arm imaging system, acquiring a series of projected images independent of said phases at successive respective known times in all phases of the uninterrupted external periodic motion represented in the generated positioning information;
    storing the acquired series of projected images in an image data set with position information;
    constructing a three-dimensional image, defined by three orthogonal spatial directions from images in the data set for a particular position of the subject in said uninterrupted external periodic motion;
    repeating the construction of three-dimensional images from images in the data set for each position of the subject in the uninterrupted periodic motion represented in the generated position information, thereby forming a three-dimensional image set; and
    combining the images of the three-dimensional image set into a four-dimensional image using said three orthogonal spatial directions as three of the four dimensions and using said uninterrupted external periodic motion as a running variable for a fourth of the four dimensions.

2. The method according to claim 1, comprising employing a camera as the external position or motion sensor.

3. The method according to claim 1, comprising employing a pressure belt as the external position or motion sensor is a pressure belt.

4. A method for creating a four-dimensional image of a, subject comprising:
    from a subject exhibiting uninterrupted external periodic motion, detecting position generating positioning information representing the uninterrupted periodic external motion of the subject utilizing external position or motion sensors, said periodic motion comprising successive phases;
    triggering acquisition of a series of projected images, independently of said phases, using a C-arm imaging system, at successive respective known times in all phases the uninterrupted external periodic motion represented in the generated position information;
    associating the positioning information acquired with each of the series of projected images by a time stamp embodied each of the projected images themselves;
    storing the acquired series of projected images in an image data set with position information;
    constructing a three-dimensional image, defined by three orthogonal spatial direction from images in the data set for a particular position of the subject in said uninterrupted external periodic motion;
    repeating the construction of three-dimensional images from images in the data set for each position of the subject in the uninterrupted external periodic motion represented in the generated position information, thereby forming a three-dimensional image set; and
    combining the images of the three-dimensional image set into a four-dimensional image using said three orthogonal spatial directions as three of the four dimensions and using said uninterrupted external periodic motion as a running variable for a fourth of the four dimensions.

5. An imaging system for creating a four-dimensional image of a subject, comprising:
    a C-arm carrying a radiation source and a radiation detector configured to acquire projected images from a subject exhibiting uninterrupted external periodic motion, said periodic motion comprising successive phases;
    an external position or motion sensor configured to detect position information representing the uninterrupted periodic external motion of the subject;
    a processor having an input connected to an output of the external position or motion sensor and an input connected to an output of the radiation detector, the processor further having access to a memory store a series of said projected images is stored, each projected image being stored with appertaining position information indicating a position of the subject in said uninterrupted external periodic motion that existed when each of said projected images was acquired;

the processor being configured to construct a three-dimensional image, defined by three orthogonal spatial direction, from the stored projected images in the memory for a particular position of the subject in said uninterrupted external periodic motion, and to repeat the construction of three-dimensional images from said projected images in the memory for each position of the subject in the uninterrupted external periodic motion represented in the generated position information, to form a three-dimensional image set, and to combine the images of the three-dimensional image set into a four-dimensional image using said three orthogonal spatial directions as three of the four dimensions and using said uninterrupted external periodic motion as a running variable for a fourth of the four dimensions; and an output at which the four-dimensional image is accessible to a user.

6. The imaging system according to claim 5, wherein the external position or motion sensor is a camera.

7. The imaging system according to claim 5, wherein the external position or motion sensor is a pressure belt.

\* \* \* \* \*